United States Patent [19]

Gante et al.

[11] Patent Number: 5,561,148
[45] Date of Patent: Oct. 1, 1996

[54] ADHESION RECEPTOR ANTAGONISTS III

[75] Inventors: Joachim Gante, Darmstadt; Horst Juraszyk; Peter Raddatz, both of Seeheim; Hanns Wurziger, Darmstadt; Guido Melzer, Hofheim/Ts.; Sabine Bernotat-Danielowski, Bad Nauheim, all of Germany

[73] Assignee: Merck Patent Gesellschaft Mit Beshrankter Haftung, Darmstadt, Germany

[21] Appl. No.: 310,085

[22] Filed: Sep. 22, 1994

[30] Foreign Application Priority Data

Sep. 23, 1993 [DE] Germany ........................ 43 32 384.7

[51] Int. Cl.$^6$ ........................ C07D 263/38; A61K 31/42
[52] U.S. Cl. ........................ 514/376; 514/256; 514/340; 544/335; 546/271.4; 548/232; 548/229
[58] Field of Search .................... 514/376; 548/229

[56] References Cited

U.S. PATENT DOCUMENTS

| | | | |
|---|---|---|---|
| 4,374,990 | 2/1983 | Weber et al. | 544/376 |
| 4,602,093 | 7/1986 | Baldwin et al. | 548/336 |
| 4,970,217 | 11/1990 | Prucher et al. | 514/327 |
| 5,053,393 | 10/1991 | Tjoeng et al. | 514/18 |
| 5,232,931 | 8/1993 | Prücher et al. | 514/321 |

FOREIGN PATENT DOCUMENTS

| | | |
|---|---|---|
| 0300272 | 1/1989 | European Pat. Off. . |
| 0381033 | 8/1990 | European Pat. Off. . |
| 0443197 | 8/1991 | European Pat. Off. . |
| 0605729 | 7/1994 | European Pat. Off. . |
| 0623615 | 11/1994 | European Pat. Off. . |
| 93-22298 | 11/1993 | WIPO ........................ 548/232 |

OTHER PUBLICATIONS

"Low Molecular Weight, Non–Peptide Fibrinogen Receptor Antagonists", Alig et al., *J. Med. Chem.*, vol. 35, 1992, pp. 4393–4407.
"Potent in Vitro and in Vivo Inhibitors of Platelet Aggregation Based upon the Arg–Gly–Asp–Phe Sequence of Fibrinogen. A Proposal on the Nature of the Binding Interaction between the Arg–guanidine of RGDX Mimetics and the Platelet GP IIb–IIIa Receptor". Zablocki et al., *J. Med. Chem.*, vol. 36, 1993, pp. 1811–1819.
Y. Iwakura et al., Bulletin of the Chemical Society of Japan, "2–*Oxazolidones from Glycidyl Ether Reactions with acid Amides*", vol. 39, pp. 2490–2494 (1966).
Iwakura et al. Chem Abstr vol. 64 Entry 8163a (1961).
Iwakura et al. Chem Abstr vol. 67 Entry 108577 (1966).
Burger, "Medicinal Chemistry" 2d. Ed. Inter–Science, New York, 1960 p. 42.

*Primary Examiner*—Donald G. Daus
*Attorney, Agent, or Firm*—Millen, White, Zelano & Branigan, P.C.

[57] ABSTRACT

Novel oxazolidinone derivatives of the formula I in which $R^1$ is a phenyl radical which is unsubstituted or is monosubstituted by CN, $H_2N$—$CH_2$—, $A_2N$—$CH_2$—, $H_2N$—$C(=NH)$—, $H_2N$—$C(=NH)$—$NH$—, $H_2N$—$C(=NH)$—$NH$—$CH_2$—, $HO$—$NH$—$C(=NH)$— or $HO$—$NH$—$C(=NH)$—$NH$—, X is O, S, SO, $SO_2$, —NH— or —NA—, B is A is alkyl having from 1 to 6 C atoms, $R^2$ is H, A, Li, Na, K, $NH_4$ or benzyl, $R^3$ is H or $(CH_2)_n$—$COOR^2$, E is, in each case independently of each other, CH or N, Q is O, S or NH, m is 1, 2 or 3, and n is 0, 1, 2 or 3, and physiologically compatible salts thereof are provided, which inhibit the binding of fibrinogen to the corresponding receptor and can be used for treating thrombosis, stroke, cardiac infarction, inflammations, arteriosclerosis, osteoporosis and also tumors.

13 Claims, No Drawings

ADHESION RECEPTOR ANTAGONISTS III

SUMMARY OF THE INVENTION

The invention relates to oxazolidinone derivatives of the formula I

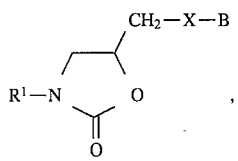

in which

R¹ is a phenyl radical which is unsubstituted or is monosubstituted by CN, $H_2N$—$CH_2$—, $A_2N$—$CH_2$—, $H_2N$—C(=NH)—, $H_2N$—C(=NH)—NH—, $H_2N$—C(=NH)—NH—$CH_2$—, HO—NH—C(=NH)— or HO—NH—C(=NH)—NH—, X is O, S, SO, $SO_2$, —NH— or —NA—, B is

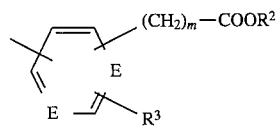

o

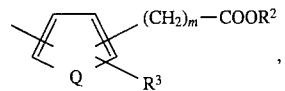

A is alkyl having from 1 to 6 C atoms,

R² is H, A, Li, Na, K, $NH_4$ or benzyl,

R³ is H or $(CH_2)_n$—$COOR^2$,

E is, in each case independently of each other, CH or N,

Q is O, S or NH, m is 1, 2 or 3, and n is 0, 1, 2 or 3, and physiologically compatible salts thereof.

EP-A1-0 381 033 discloses similar compounds.

The object underlying the invention was to provide novel compounds possessing valuable properties, in particular such compounds as can be used for preparing drugs.

This object was achieved by the invention. It has been found that the compounds of the formula I, and their solvates and salts, while being well tolerated, possess valuable pharmacological properties. In particular, they inhibit both the binding of fibrinogen, fibronectin and the von Willebrand factor to the fibrinogen receptor of the blood platelets (glycoprotein lib/Ilia) and the binding of these compounds, and of other adhesive proteins, such as vitronectin, collagen and laminin, to the corresponding receptors on the surface of various cell types. The compounds thus exert an influence on cell-cell interactions and cell-matrix interactions. In particular, they inhibit the formation of blood platelet thrombi and are useful for treating thromboses, stroke, cardiac infarction, inflammations and arteriosclerosis.

The compounds are also suitable as anti-microbial active substances which are able to prevent infections, for example, those initiated by bacteria, fungi or yeasts. The substances can therefore preferably be given as accompanying anti-microbial active substances, when organisms are subjected to interventions in which exogenous, for example, biomaterials, implants, catheters, or pacemakers, are employed. They act as antiseptics. Anti-microbial activity of the compounds can be demonstrated by the procedure described by P. Valentin-Weigand et al., Infection and Immunity, 2851–2855 (1988).

In addition to this, the compounds have an effect on tumor cells by preventing these cells from metastasizing. They are, therefore, also useful as anti-tumor agents.

There is evidence that tumor cells spreading from a solid tumor into the vasculature are carried by microthrombi and thus are protected from being detected by cells of the immune system. The second step of attachment to the vessel wall seems to be facilitated by microthrombi as well. Since the formation of thrombi is mediated by fibrinogen binding to the fibrinogen receptor (glycoprotein llb/IIIa) on activated platelets, fibrinogen-binding inhibitors are expected to be effective as antimetastatics.

Also, since fibrinogen-binding inhibitors are ligands with fibrinogen receptor on platelets, they can be used as diagnostic tools for detection and localization of thrombi in the vascular in vivo. Thus, for example, in accordance with known procedures, the fibrinogen-binding inhibitors can be labeled with a signal-generating or detectable moiety whereby, once the labeled fibrinogen-binding inhibitor is bound to a fibrinogen receptor on platelets, it is possible to detect and locate thrombi.

Fibrinogen-binding inhibitors are also very effective as research tools for studying the metabolism of platelets in the different activation states or intracellular signalling mechanisms of the fibrinogen receptor. For example, as described above, fibrinogen-binding inhibitor can be labeled with a signal-generative or detectable moiety. The fibrinogen-binding inhibitor-signal generating/detectable moiety conjugate can then be employed in vitro as a research tool. By binding the conjugate to fibrinogen receptors, it is possible to monitor and study the metabolism of platelets, as well as the activation states and signalling mechanisms of the fibrinogen receptors.

Furthermore, the compounds are suitable for the treatment and the prophylaxis of osteolytic disorders, in particular, osteoporosis, and restenosis after angioplasty. They can also be used in a supportive role in wound healing processes and have anti-angiogenetic properties.

The properties of the compounds can be demonstrated using methods which are described in EP-A 1-0 462 960. The inhibition of the binding of fibrinogen to the fibrinogen receptor can be demonstrated by the method which is given in EP-A1-0 381 033. The effect of inhibiting blood-platelet aggregation can be demonstrated in vitro using the method of Born (Nature, 4832:927–929 (1962)).

The invention furthermore relates to a process for preparing a compound of the given formula I, as well as its salts, which process is characterized in that a compound of the formula II

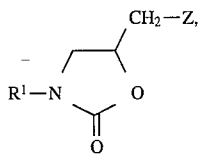

in which

R¹ has the meaning given in claim 1, and

Z is Cl, Br, I, OH or a reactive esterified OH group, is reacted with a compound of the formula III in which B has the above-mentioned meaning, and Y is OH, SH, $NH_2$, NAH or a salt-like radical which can be derived from OH or SH, or in that a compound of the formula IV

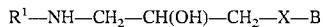

in which

R$^1$, B and X have the above-mentioned meanings, or one of its reactive derivatives, is reacted with a reactive derivative of carbonic acid, or in that, in order to prepare a guanidino compound of the formula I (R$^1$=a phenyl radical which is monosubstituted by H$_2$N—C(=NH)—NH—), an amino compound corresponding to the formula I, which compound, however, contains an aminophenyl group in place of the radical R$^1$, is treated with an amidinating agent, or in that a compound of the formula I is liberated from one of its functional derivatives by treatment with a solvolyzing or hydrogenolyzing agent, and/or in that, in a compound of the formula I, one or both of the radicals R$^1$ and/or B is/are converted into (an) other radical(s) R$^1$ and/or B, and/or a compound of the formula I is converted into one of its salts by treatment with an acid or a base.

The compounds of the formula I possess at least one chiral center and can therefore appear in several enantiomeric forms. All of these forms (for example, D and L forms) and their mixtures (for example, the DL forms) are included in the formula I.

Both hereinbefore and hereinafter, the radicals and/or parameters B, X, R$^1$ to R$^3$, A, E, Q, Y, Z, m and n have the meanings given in the formulae I, II or III, unless expressly indicated otherwise.

In the above formulae, the group A has 1–6, preferably 1, 2, 3 or 4, C atoms. Specifically, A, is preferably methyl, ethyl, propyl, isopropyl, butyl, isobutyl, sec-butyl or tert-butyl, and, in addition, pentyl, 1-, 2- or 3-methyl-butyl, 1,1-, 1,2- or 2,2-dimethylpropyl, 1-ethylpropyl, hexyl or 1-, 2-, 3- or 4-methylpentyl.

X is preferably O, but also S, NH or NA, for example, N—CH$_3$, or even SO and SO$_2$.

R$^1$ is preferably a phenyl radical which is substituted, as indicated above, in the 4-position or else in the 2- or 3-positions; specific preference is given to 2-, 3- or, in particular, 4-amidinophenyl; 2-, 3- or 4-aminomethylphenyl; 2-, 3- or 4-guanidinomethylphenyl; 2-, 3- or 4-cyanophenyl or else 2-, 3- or 4-N-alkylaminomethylphenyl, with, in these instances, alkyl preferably being methyl or ethyl.

B is preferably monosubstituted or bisubstituted phenyl or pyrrolyl, or else monosubstituted thienyl, or else pyridinyl, furanyl or pyrimidinyl in unsubstituted or substituted form, with the said substituents being possible. Specific preference is given to B being 2-, 3- or 4-carboxymethyl-, 2-, 3- or 4-methoxycarbonyl-, or-ethoxycarbonyl-phenyl, as well as, preferably, 2-carboxymethylthien-4-yl, 2-carboxymethylpyrrol-4-yl, 3-carboxymethylpyrrol-4-yl, 2,5-dicarboxymethyl- or 2,3-dicarboxymethylpyrrol-4-yl, 2-carboxymethyl-3-carboxy- or 2-carboxymethyl-5-carboxypyrrol-4-yl or 2,3-, 2,4-, 2,5-, 2,6-, 3,4- or 3,5-dicarboxymethylphenyl, and preferably also the methyl or ethyl esters of the aforementioned preferred radicals and also the Li, Na, K or ammonium salt radicals which can be derived therefrom.

R$^2$ is preferably hydrogen, A or Na, while R$^3$ is particularly preferably H or carboxymethyl. E is preferably CH and Q is preferably S or NH.

The parameters m and n are preferably 1, but also 2 or 3. In addition to this, the variable n can also be O.

Those compounds of the formula I are preferred in which at least one of the given radicals, groups and/or parameters has one of the given preferred meanings. Some groups of preferred compounds are those of the formulae Ia to Ij, which conform to the formula I but in which in Ia, X is 0;

in Ib, X is 0, and

B is 2-, 3- or 4-carboxymethylphenyl;

in Ic, X is 0, and

R$^1$ is 2-, 3- or 4-amidinophenyl;

in Id, X is NH or NA, and

R$^1$ is 2-, 3- or 4-amidinophenyl;

in Ie, X is S, and

R$^1$ is 2-, 3- or 4-amidinophenyl;

in If, X is 0, and

B is 2,3-, 2,4-, 2,5-, 2,6-, 3,4- or 3,5-dicarboxymethylphenyl;

in Ig, X is 0, and

B is 2-carboxymethyl- or 3-carboxymethyl-thien-4-yl or-pyrrol-4-yl;

in Ih, X is 0, and

B is 2,3- or 2,5-dicarboxymethyl- or 2-carboxymethyl-3-carboxy- or 2-carboxymethyl- 5-carboxypyrrol-4-yl;

in Ii, X is 0,

B is 2-, 3- or 4-carboxyphenyl, and

R$^1$ is 2-, 3- or 4-amidinophenyl;

in Ij, X is 0,

B is 2,3-, 2,4-, 2,5-, 2,6-, 3,4- or 3,5-dicarboxymethylphenyl, and

R$^1$ is 2-, 3- or 4-amidinophenyl.

In addition to this, compounds are preferred which conform perse to the formulae Ia to Ij but in which the carboxyl group of the radical B is replaced by a methoxycarbonyl or ethoxycarbonyl group.

The compounds of the formula I, and also the starting compounds for their preparation, are otherwise prepared by methods, which are known per se as described in the literature (for example, in the standard works such as Houben-Weyl, Methoden der organischen Chemie (Methods of Organic Chemistry), Georg-Thieme-Verlag, Stuttgart; as well as EP-A1-0381033 which corresponds to U.S. Pat. Nos. 5,084,466 and 5,256,812, and EP-A1-0462960which corresponds to U.S. Pat. No. 5,053,393), specifically using reaction conditions which are known and are suitable for the reactions mentioned. In addition, alternative methods which are known per se will be evident to the skilled worker.

If desired, the starting compounds may also be formed in situ, so that they are not isolated from the reaction mixture but, instead, further reacted immediately to form the compounds of the formula I.

The compounds of the formula I can be obtained by liberating them from their functional derivatives by solvolysis, in particular hydrolysis, or by hydrogenolysis. Those starting compounds are preferred for the solvolysis or hydrogenolysis which otherwise conform to the formula I but which contain corresponding protected amino and/or hydroxyl groups in place of one or more free amino and/or hydroxyl groups, preferably those which carry an amino protective group in place of a H atom which is bonded to an N atom, in particular those which carry an R'—N group, in which R' is an amino protective group, in place of an HN group, and/or those which carry a hydroxyl protective group in place of the H atom of a hydroxyl group, for example, those which conform to the formula I but which carry a —COOR" group, in which R" is a hydroxyl protective group, in place of a —COOH group.

Several—identical or different—protected amino and/or hydroxyl groups may be present in the molecule of the starting compound. If the protective groups which are present differ from each other, they may, in many cases, be eliminated selectively.

The expression "amino protective group" is well known and refers to groups which are suitable for protecting (blocking) an amino group from chemical reactions but which can easily be removed once the desired chemical reaction has been carried out at another site in the molecule. Especially typical of such groups are unsubstituted or substituted acyl, aryl (e.g., 2,4-dinitrophenyl (DNP)), aralkoxymethyl (e.g., benzyloxymethyl (BOM)) or aralkyl groups (e.g., benzyl, 4-nitrobenzyl or triphenylmethyl). Since the amino protective groups are removed after the desired reaction (or sequence of reactions), their nature and size is otherwise not critical; nevertheless, those having 1–20, in particular 1–8, C atoms are preferred. In connection with the present process, the expression "acyl group" is to be interpreted in its widest sense. It embraces acyl groups derived from aliphatic, araliphatic, aromatic or heterocyclic carboxylic acids or sulfonic acids, and, in particular, alkoxycarbonyl, aryloxy-carbonyl and, especially, aralkoxycarbonyl groups. Examples of acyl groups of this kind are alkanoyl, such as acetyl, propionyl or butyryl; aralkanoyl, such as phenylacetyl; aroyl, such as benzoyl or toluoyl; aryloxyalkanoyl, such as phenoxyacetyl; alkoxycarbonyl, such as methoxycarbonyl, ethoxycarbonyl, 2,2,2-trichloroethoxycarbonyl, isopropoxycarbonyl, tert-butoxycarbonyl (BOC) or 2-iodoethoxycarbonyl; aralkyloxycarbonyl, such as benzyloxycarbonyl (CBZ), 4-methoxybenzyloxycarbonyl or 9-fluorenylmethoxycarbonyl (FMOC). Amino protective groups which are preferred are BOC, DNP and BOM, and, in addition, CBZ, benzyl and acetyl.

The expression "hydroxyl protective group" is likewise well known and refers to groups which are suitable for protecting a hydroxyl group from chemical reactions but which are readily removed once the desired chemical reaction has been carried out at another site in the molecule. Typical of such groups are the above-mentioned unsubstituted or substituted aryl, aralkyl or acyl groups, as are alkyl groups. The nature and size of the hydroxyl protective groups is not critical since they can be removed once again after the desired chemical reaction or sequence of reactions; groups having 1–20, in particular 1–10, C atoms are preferred. Examples of hydroxyl protective groups are, inter alia, tert-butyl, benzyl, p-nitrobenzoyl, p-toluenesulfonyl and acetyl, with benzyl and acetyl being particularly preferred.

The functional derivatives of the compounds of the formula I, which are to be used as starting compounds, may be prepared by customary methods as described, for example, in the said standard works and patent applications, for example, by reacting compounds which conform to the formulae II and III, with, however, at least one of these compounds containing a protective group in place of a H atom.

The liberation of the compounds of the formula I from their functional derivatives is, for example, achieved—depending on the protective group used—with strong acids, expediently with trifluoroacetic acid or perchloric acid, but also with other strong inorganic acids, such as hydrochloric acid or sulfuric acid, strong organic carboxylic acids, such as benzenesulfonic acid or p-toluenesulfonic acid. It is possible, but not always necessary, for an inert solvent to be present in addition.

Inert solvents which are suitable are preferably organic, for example, carboxylic acids, such as acetic acid, ethers, such as tetrahydrofuran or dioxane, amides, such as dimethylformamides (DMF), halogenated carbohydrates, such as dichloromethane, and, in addition, alcohols, such as methanol, ethanol or isopropanol and also water. In addition, mixtures of the above-mentioned solvents are suitable. Trifluoroacetic acid is preferably used in excess without the addition of any further solvent, perchloric acid in the form of a mixture of acetic acid and 70% perchloric acid in the ratio of 9:1. The reaction temperatures for the cleavage are expediently about 0°–50°, preferably 15°–30° (room temperature).

The BOC group can be eliminated, e.g., preferably using 40% trifluoroacetic acid in dichloromethane or using, preferably, about 3–5N HCl in dioxane at, preferably, 15°–60°, and the FMOC group using, preferably, an approximately 5–20% solution of dimethylamine, diethylamine or piperidine in DMF at, preferably, 15°–50°. Elimination of the DNP group is also achieved, for example, using, preferably, an approximately 3–10% solution of 2-mercapto-ethanol in DMF/water at, preferably, 15°–30°.

Protective groups which can be removed by hydrogenolysis (e.g., BOM, CBZ or benzyl) can be eliminated, for example, by treating with hydrogen in the presence of a catalyst (e.g., a precious metal catalyst such as palladium, expediently on a support such as carbon). Suitable solvents in this case are those indicated above, in particular, for example, alcohols, such as methanol or ethanol, or amides, such as DMF. As a rule, a hydrogenolysis is carried out at temperatures of, preferably, about 0°–100° and under pressures of, preferably, about 1–200 bar, preferably at 20°–30° and at, preferably, 1–10 bar. Hydrogenolysis of the CBZ group is readily achieved, for example, on, preferably, 5–10% Pd-C in methanol at, preferably, 20°–30°.

Compounds of the formula I can also, preferably, be obtained by reacting an oxazolidinone of the formula II with a compound of the formula III. For this, use is expediently made of the methods, which are known per se, of esterification or of the N-alkylation of amines.

The leaving group Z of the formula II is preferably Cl, Br, I, $C_1$–$C_6$-alkylsulfonyloxy, such as methanesulfonyloxy or ethanesulfonyloxy, or $C_6$–$C_{10}$-arylsulfonyloxy, such as benzenesulfonyloxy, p-toluenesulfonyloxy or 1- or 2-naphthalenesulfonyloxy.

The reaction is preferably carried out in the presence of an additional base, for example, an alkali metal or alkaline earth metal hydroxide or carbonate, such as sodium, potassium or calcium hydroxide, or sodium, potassium or calcium carbonate, in an inert solvent, for example, a halogenated hydrocarbon, such as dichloromethane, an ether, such as THF or dioxane, an amide, such as DMF or dimethylacetamide, or a nitrile, such as acetonitrile, at temperatures of, preferably, about –10°–200°, especially 0°–120°. If the leaving group Z is different from I, it is advisable to add an iodide such as potassium iodide.

As a rule, the starting compounds of the formula II are novel. They can be prepared, for example, by reacting a substituted aniline of the formula $R^1$—$NH_2$, in which $R^1$ has the given meaning, with a compound of the formula $R^5CH_2$—$CHR^6$—$CH_2OH$ (in which $R^5$ is Z, $R^6$ is $OR^7$, $R^7$ is a protective group, or $R^5$ and $R^6$ together are also O) to yield a compound of the formula $R^1$—NH—$CH_2$—$CHR^8$—$CH_2OH$ (in which $R^8$ is $OR^7$ or OH), where appropriate eliminating the protective group $R^7$ to yield compounds of the formula $R^1$—NH—$CH_2$—CH(OH)—$CH_2OH$, reacting with a derivative of carbonic acid, such as diethyl carbonate, to yield 3—$R^1$—5-hydroxymethyl-2-oxazolidinones, and converting the hydroxymethyl group into a $CH_2Z$ group, for example, using $SOCl_2$, $SOBr_2$, methanesulfonyl chloride or p-toluenesulfonyl chloride. As a rule, the compounds of the formula Y-B (III) are known or can be prepared in analogy with known compounds.

Compounds of the formula I can also be obtained by reacting a compound of the formula IV (or a reactive derivative thereof) with a reactive derivative of carbonic acid.

Suitable carbonic acid derivatives are, in particular, dialkyl carbonates, such as diethyl carbonate, and also alkyl chloroformates, such as ethyl chloroformate. The carbonic acid derivative, which is expediently employed in excess, preferably also serves as solvent or suspending agent. However, one of the given solvents can also be present as long as it is inert in this reaction. It is furthermore advisable to add a base, in particular an alkali metal alcoholate such as potassium tert-butoxide. Reaction temperatures of preferably 0°–150°, especially 70°–120°, are expediently employed.

As a rule, the starting compounds of the formula IV are novel. They can be obtained, for example, by functionalizing the above-mentioned compounds of the formula $R^1$—NH—$CH_2$—CH(OH)—$CH_2OH$ to yield compounds of the formula $R^1$—NH—$CH_2$—CH(OH)—$CH_2$—Z and reacting with compounds of the formula B-Y (III).

In order to prepare compounds of the formula I in which $R^1$ is a guanidinophenyl group, a corresponding aminophenyl compound can be treated with an amidinating agent. 1-Amidino-3,5-dimethylpyrazole is preferred as the amidinating agent, especially when it is employed in the form of its nitrate. The reaction is expediently carried out with addition of a base, such as triethylamine or ethyldiisopropylamine, in an inert solvent or solvent mixture, e.g., water/dioxane, at temperatures of preferably 0°–120°, especially 60°–120°.

It is furthermore possible, in a compound of the formula I, to convert one or both of the radicals $R^1$ and/or B into (an) other radical(s) $R^1$ and/or B.

In particular, cyano groups can be reduced to aminomethyl groups or converted into amidino groups, carboxyl groups can be esterified, ester groups can be cleaved, benzyl groups can be removed hydrogenolytically, and aminomethyl groups can be converted into guanidinomethyl groups.

Cyano groups can expediently be reduced to aminomethyl groups by catalytic hydrogenation, e.g., on Raney nickel at temperatures of preferably 0°–100°, especially 10°–30°, and under pressures of 1–200 bar, preferably under standard pressure, in an inert solvent, e.g., in a lower alcohol, such as methanol or ethanol, expediently in the presence of ammonia. If the reaction is carried out, for example, at about 20° and 1 bar, benzyl ester or N-benzyl groups present in the starting material are then preserved. If it is desired to cleave these groups hydrogenolytically, it is then expedient to use a precious metal catalyst, preferably Pd-carbon, it being possible to add an acid such as acetic acid and also water to the solution.

In order to prepare an amidine of formula I ($R^1$=amidinophenyl), ammonia can be added to a nitrile of the formula I ($R^1$=cyanophenyl). The addition is preferably effected in several steps by, in a known manner, (a) converting the nitrile with $H_2S$ into a thioamide which is converted with an alkylating agent, e.g., $CH_3I$, into the corresponding S-alkylimidothio ester which, for its part, reacts with $NH_3$ to yield the amidine, (b) converting the nitrile with an alcohol, e.g., ethanol, in the presence of HCl into the corresponding imido ester and treating the latter with ammonia, or (c) reacting the nitrile with lithium bis(trimethylsilyl)amide and subsequently hydrolyzing the product.

The corresponding N-hydroxyamidines of the formula I ($R^1$=phenyl substituted by HO—NH—C(—NH)—) can be obtained in an analogous manner from the nitriles if procedures (a) or (b) are followed but using hydroxylamine instead of ammonia.

For the esterification, an acid of the formula I ($R^2$=H) can be treated with an excess of an alcohol of the formula $R^2$—OH ($R^2$=A or benzyl), expediently in the presence of a strong acid, such as hydrochloric acid or sulfuric acid, at temperature of preferably 0°–100°, especially 20°–50°.

Conversely, an ester of the formula I ($R^2$=A or benzyl) can be converted into the corresponding acid of the formula I ($R^2$=H), expediently by solvolysis in accordance with one of the above-mentioned methods, e.g., using NaOH or KOH in water/dioxane at temperatures of preferably 0°–40°, especially 10°–30°.

A base of the formula I can be converted with an acid into the associated acid addition salt. Acids which are especially suitable for this reaction are those which yield physiologically harmless salts. Thus, inorganic acids may be used, for example, sulfuric acid, nitric acid, hydrohalic acids, such as hydrochloric acid or hydrobromic acid, phosphoric acids, such as orthophosphoric acid, or sulfamic acid, and, in addition, organic acids, in particular aliphatic, alicyclic, araliphatic, aromatic or heterocyclic monobasic or polybasic carboxylic, sulfonic or sulfuric acids, e.g., formic acid, acetic acid, trifluoroacetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methanesulfonic acid, ethanesulfonic acid, ethanedisulfonic acid, 2-hydroxyethanesulfonic acid, benzenesulfonic acid, p-toluenesulfonic acid, naphthalenemonosulfonic acid, naphthalenedisulfonic acid and laurylsulfuric acid. Salts with physiologically unacceptable acids, e.g., picrates, may be used for isolating and/or purifying the compounds of the formula I.

If desired, the free bases of the formula I can be liberated from their salts by treatment with strong bases such as sodium or potassium hydroxide, or sodium or potassium carbonate.

It is also possible to convert carboxylic acids of the formula I ($R^2$=H) into their metal or ammonium salts, e.g., their sodium, potassium or calcium salts, by reaction with corresponding bases.

The compounds of the formula I contain one or more chiral centers and can therefore be present in racemic or in optically active form. Racemates which have been obtained can be resolved mechanically or chemically into the enantiomers using methods which are known per se. Diastereomers are preferably formed from the racemic mixture by reaction with an optically active resolving agent. Suitable resolving agents are, for example, optically active acids, such as the D and L forms of tartaric acid, diacetyltartaric acid, dibenzoyltartaric acid, mandelic acid, malic acid or lactic acid, or the various optically active camphorsulfonic acids, such as β-camphorsulfonic acid.

It is also advantageous to resolve the enantiomers using a column which is packed with an optically active resolving agent (e.g., dinitrobenzoylphenylglycine); a mixture of hexane/isopropanol/acetonitrile (8:2:1) is an example of a suitable eluent.

It is also possible, naturally, to obtain optically active compounds of the formula in accordance with the above-described methods by using starting compounds (e.g., those of the formula II) which are already optically active.

The novel compounds of the formula I and their physiologically harmless salts can be used for producing pharmaceutical preparations by bringing them into a suitable dosage form together with at least one excipient or auxiliary substance and, if desired, together with one or more additional active compound(s). The preparations thus obtained can be employed as medicaments in human or veterinary medicine. Suitable excipient substances are organic or inorganic substances which are suitable for enteral (e.g., oral or rectal) or parenteral administration or for administration in the form of an inhalation spray and which do not react with the novel compounds, for example, water, vegetable oils, benzyl alcohols, polyethylene glycols, glycerol triacetate and other fatty acid glycerides, gelatin, soya lecithin, carbohydrates, such as lactose or starch, magnesium stearate, talc and cellulose. Tablets, coated tablets, capsules, syrups, juices or drops are used, in particular, for oral administration; film tablets and capsules having enteric coatings or capsule shells are especially of interest. Suppositories are used for rectal administration, and solutions, preferably oily or aqueous solutions, and, in addition, suspensions, emulsions or implants are used for parenteral administration.

For administration as an inhalation spray, sprays can be used which contain the active compound either dissolved or suspended in a propellant gas mixture. The active compound is expediently used in this context in micronized form, it being possible for one or more additional physiologically tolerated solvents, e.g., ethanol, to be present. Inhalation solutions can be administered with the aid of customary inhalers. The novel compounds can also be lyophilized and the resulting lyophilizates used, for example, for producing injection preparations. The preparations indicated can be sterilized and/or can contain auxiliary substances, such as preservatives, stabilizers and/or wetting agents, emulsifiers, salts for influencing the osmotic pressure, buffering substances, colorants and/or flavorings, If desired, they can also contain one or more additional active compounds, e.g., one or more vitamins.

As a rule, the substances according to the invention are administered in analogy with other known, commercially available, drugs, in particular, however, in analogy with the compounds described in EP-A-459256which corresponds to U.S. Pat. No. 5,232,931, preferably in dosages of about 5 mg–1 g, in particular 50–500 mg, per dosage unit. The daily dosage is preferably about 0.1–20 g/kg, in particular 1–10 mg/kg, of body weight. However, the special dose for each particular patient depends on a wide variety of factors, for example, on the activity of the special compound employed, on the age, body weight, general state of health and sex, on the food, on the time and route of administration, on speed of excretion, on the combination of drugs being employed, and on the severity of the particular disease to which the therapy applies. Oral administration is preferred.

Suitable preparations for using the compounds as antimicrobial agents are, for example, injection vials, ampoules, solutions, and capsules. Carriers, excipients, and further additives are mentioned in Examples A–E. The amount of the inventive compound in the antimicrobial agents is preferably about 0.05–500 mg per dosage unit.

Hereinbefore and hereinafter, all temperatures are indicated in °C. In the following examples, "customary working-up" denotes: water is added if necessary, the pH is adjusted to values of between 2 and 8, depending on the constitution of the final product, the mixture is extracted with ethyl acetate or dichloromethane, the phases are separated, the organic phase is dried over sodium sulfate and concentrated by evaporation, and the product is purified by chromatography on silica gel and/or by crystallization.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, unless otherwise indicated, all parts and percentages are by weight.

The entire disclosure of all applications, patents and publications, cited above and below, and of corresponding German application P 43 32 384.7, filed Sep. 23, 1993, are hereby incorporated by reference.

EXAMPLES

Example 1

1 Equivalent of NaH is added to a solution of 1.7 g of Na p-methoxycarbonylmethylphenoxide (obtainable by converting p-hydroxybenzyl cyanide into the corresponding carboxylic acid, esterifying with methanol to give p-methoxycarbonylmethylphenol and subsequently converting the latter into the phenoxide) in 20 ml of dimethylformamide (DMF), and the mixture is stirred at room temperature for 30 min. After that, 3.0 g of 3-p-cyanophenyl-5-methanesulfonyloxymethyloxazolidin-2-one ("A") (obtainable by reacting p-aminobenzonitrile with 2,3-epoxypropan-1-ol to give p-(N-2,3-dihydroxypropylamino)benzonitrile, reacting the latter with diethyl carbonate in the presence of K tert-butoxide to give 3-p-cyanophenyl-5-hydroxymethyloxazolidin-2-one and subsequently esterifying the latter with methanesulfone chloride), dissolved in 10 ml of DMF, are added and the mixture is once again stirred at room temperature for 15 min. Following removal of the solvent, and the customary working-up, 3-p-cyanophenyl-5-(p-methoxycarbonylmethylphenoxymethyl)oxazolidin-2-one is obtained, M.p. 114°–115°.

The following compounds are obtained in an analogous manner by reacting "A"
with Na o-methoxycarbonylmethylphenoxide:
  3-p-cyanophenyl-5-(o-methoxycarbonylmethylphenoxymethyl)oxazolidin-2-one, $M^{+}+1=366$;
with Na m-methoxycarbonylmethylphenoxide:
  3-p-cyanophenyl-5-(m-methoxycarbonylmethylphenoxymethyl)oxazolidin-2-one, M.p. 129°–130°;
with Na 2,4-bis(methoxycarbonylmethyl)phenoxide:
  3-p-cyanophenyl-5-[2,4-bis(methoxycarbonylmethyl)phenoxymethyl]oxazolidin-2-one;
with Na 2,5-bis(methoxycarbonylmethyl)phenoxide:
  3-p-cyanophenyl-5-[2,5-bis(methoxycarbonylmethyl)phenoxymethyl]oxazolidin-2-one;
with Na 2,6-bis(methoxycarbonylmethyl)phenoxide:
  3-p-cyanophenyl-5-[2,6-bis(methoxycarbonylmethyl)phenoxymethyl]oxazolidin-2-one;
with Na 3,4-bis(methoxycarbonylmethyl)phenoxide:
  3-p-cyanophenyl-5-[3,4-bis(methoxycarbonylmethyl)phenoxymethyl]oxazolidin-2-one;
with Na 3,5-bis(methoxycarbonylmethyl)phenoxide:
  3-p-cyanophenyl-5-[3,5-bis(methoxycarbonylmethyl)phenoxymethyl]oxazolidin-2-one;
with 2-methoxycarbonylmethyl-4-hydroxythiophene Na salt:
  3-p-cyanophenyl-5-(2-methoxycarbonylmethylthien-4-yloxymethyl)oxazolidin-2-one;
with 3-methoxycarbonylmethyl-4-hydroxythiophene Na salt:
  3-p-cyanophenyl-5-(3-methoxycarbonylmethylthien-4-yloxymethyl)oxazolidin-2-one;

with 2-methoxycarbonylmethyl-3-hydroxythiophene Na salt:
3-p-cyanophenyl-5-(2-methoxycarbonylmethylthien-3-yloxymethyl)oxazolidin-2-one;
with 2-methoxycarbonylmethyl-4-hydroxypyrrole Na salt:
3-p-cyanophenyl-5-(2-methoxycarbonylmethylpyrrol-4-yloxymethyl)oxazolidin-2-one;
with 3-methoxycarbonylmethyl-4-hydroxypyrrole Na salt:
3-p-cyanophenyl-5-(3-methoxycarbonylmethylpyrrol-4-yloxymethyl)oxazolidin-2-one;
with 2-methoxycarbonylmethyl-3-carboxy-4-hydroxypyrrole Na salt:
3-p-cyanophenyl-5-(2-methoxycarbonylmethyl-3-carboxypyrrol-4-yloxymethyl)oxazolidin-2-one;
with 2-carboxy-3-hydroxy-5-methoxycarbonylmethylpyrrole Na salt:
3-p-cyanophenyl-5-(2-carboxy-5-methoxycarbonylmethylpyrrol-3-yloxymethyl)oxazolidin-2-one.

Example 2

A solution of 0.9 g of 3-p-cyanophenyl-5-(p-methoxycarbonylmethylphenoxymethyl)oxazolidin-2-one (M.p. 114°–115°) in 40 ml of a 10% methanolic solution of $NH_3$ is hydrogenated on 0.6 g of Raney Ni at room temperature and at 1 bar until $H_2$ uptake is complete. Following filtration and concentration by evaporation, the customary working-up gives 3-p-aminomethylphenyl-5-(p-methoxycarbonylmethylphenoxymethyl)oxazolidin-2-one.

The following compounds are obtained in an analogous manner by hydrogenating the corresponding nitriles:

3-p-aminomethylphenyl-5-(o-methoxycarbonylmethylphenoxymethyl)-oxazolidin-2-one;

3-p-aminomethylphenyl-5-(m-methoxycarbonylmethylphenoxymethyl)-oxazolidin-2-one;

3-p-aminomethylphenyl-5-[2,4-bis(methoxycarbonylmethyl)phenoxymethyl]oxazolidin-2-one;

3-p-aminomethylphenyl-5-[2,5-bis(methoxycarbonylmethyl)phenoxymethyl]oxazolidin-2-one;

3-p-aminomethylphenyl-5-[2,6-bis(methoxycarbonylmethyl)phenoxymethyl]oxazolidin-2-one;

3-p-aminomethylphenyl-5-[3,4-bis(methoxycarbonylmethyl)phenoxymethyl]oxazolidin-2-one;

3-p-aminomethylphenyl-5-[3,5-bis(methoxycarbonylmethyl)phenoxymethyl]oxazolidin-2-one;

3-p-aminomethylphenyl-5-(2-methoxycarbonylmethylthien-4-yloxymethyl)oxazolidin-2-one;

3-p-aminomethylphenyl-5-(3-methoxycarbonylmethylthien-4-yloxymethyl)oxazolidin-2-one;

3-p-aminomethylphenyl-5-(2-methoxycarbonylmethylthien-3-yloxymethyl)oxazolidin-2-one;

3-p-aminomethylphenyl-5-(2-methoxycarbonylmethylpyrrol-4-yloxymethyl)oxazolidin-2-one;

3-p-aminomethylphenyl-5-(3-methoxycarbonylmethylpyrrol-4-yloxymethyl)oxazolidin-2-one;

3-p-aminomethylphenyl-5-(2-methoxycarbonylmethyl-3-carboxypyrrol-4-yloxymethyl)oxazolidin-2-one;

3-p-aminomethylphenyl-5-(2-carboxy-5-methoxycarbonylmethylpyrrol-3-yloxymethyl)oxazolidin-2-one.

Example 3

2.4 g of 3-p-aminomethylphenyl-5-(p-methoxycarbonylmethylphenoxymethyl)oxazolidin-2-one are dissolved in 20 ml of dichloromethane, 12 ml of trifluoroacetic acid are added, and the mixture is stirred at room temperature for 20 min. After concentrating by evaporation, and after the customary working-up, 3-p-aminomethylphenyl-5-(p-carboxymethylphenoxymethyl)oxazolidin-2-one is obtained.

The following carboxylic acids are obtained in an analogous manner by hydrolyzing the corresponding esters:

3-p-cyanophenyl-5-(p-carboxymethylphenoxymethyl)oxazolidin-2-one;

3-p-cyanophenyl-5-(o-carboxymethylphenoxymethyl)oxazolidin-2-one;

3-p-cyanophenyl-5-(m-carboxymethylphenoxymethyl)oxazolidin-2-one;

3-p-cyanophenyl-5-[2,4-bis(carboxymethyl)phenoxymethyl]oxazolidin-2-one;

3-p-cyanophenyl-5-[2,5-bis(carboxymethyl)phenoxymethyl]oxazolidin-2-one;

3-p-cyanophenyl-5-[2,6-bis(carboxymethyl)phenoxymethyl]oxazolidin-2-one;

3-p-cyanophenylo5-[3,4-bis(carboxymethyl)phenoxymethyl]oxazolidin-2-one;

3-p-cyanophenyl-5-[3,5-bis(carboxymethyl)phenoxymethyl]oxazolidin-2-one;

3-p-cyanophenyl-5-(2-carboxymethylthien-4-yloxymethyl)oxazolidin-2-one;

3-p-cyanophenyl-5-(3-carboxymethylthien-4-yloxymethyl)oxazolidin-2-one;

3-p-cyanophenyl-5-(2-carboxymethylthien-3-yloxymethyl)oxazolidin-2-one;

3-p-cyanophenyl-5- (2-carboxymethylpyrrol-4-yloxymethyl)oxazolidin-2-one;

3-p-cyanophenyl-5-(3-carboxymethylpyrrol-4-yloxymethyl)oxazolidin-2-one;

3-p-cyanophenyl-5-(2-carboxymethyl-3-carboxypyrrol-4-yloxymethyl)oxazolidin-2-one;

3-p-cyanophenyl-5-(2-carboxy-5-carboxymethylpyrrol-3-yloxymethyl)oxazolidin-2-one;

3-p-aminomethylphenyl-5-(p-carboxymethylphenoxymethyl)oxazolidin-2-one;

3-p-aminomethylphenyl-5-(o-carboxymethylphenoxymethyl)oxazolidin-2-one;

3-p-aminomethylphenyl-5-(m-carboxymethylphenoxymethyl)oxazolidin-2-one;

3-p-aminomethylphenyl-5-[2,4-bis(carboxymethyl)phenoxymethyl]oxazolidin-2-one;

3-p-aminomethylphenyl-5-[2,5-bis(carboxymethyl)phenoxymethyl]oxazolidin-2-one;

3-p-aminomethylphenyl-5-[2,6-bis(carboxymethyl)phenoxymethyl]oxazolidin-2-one;

3-p-aminomethylphenyl-5-[3,4-bis(carboxymethyl)phenoxymethyl]oxazolidin-2-one;

3-p-aminomethylphenyl-5-[3,5-bis(carboxymethyl)phenoxymethyl]oxazolidin-2-one;

3-p-aminomethylphenyl-5-(2-carboxymethylthien-4-yloxymethyl)oxazolidin-2-one;

3-p-aminomethylphenyl-5-(3-carboxymethylthien-4-yloxymethyl)oxazolidin-2-one;

3-p-aminomethylphenyl-5-(2-carboxymethylthien-3-yloxymethyl)oxazolidin-2-one;

3-p-aminomethylphenyl-5-(2-carboxymethylpyrrol-4-yloxymethyl)oxazolidin-2-one;

3-p-aminomethylphenyl-5-(3-carboxymethylpyrrol-4-yloxymethyl)oxazolidin-2-one;

3-p-aminomethylphenyl-5-(2-carboxymethyl-3-carboxypyrrol-4-yl oxymethyl)oxazolidin-2-one;

3-p-aminomethylphenyl-5-(2-carboxy-5-carboxymethylpyrrol-3-yloxymethyl)oxazolidin-2-one.

Example 4

20 ml of a 20% solution of NaOH are added to a solution of 0.6 g of 3-p-aminomethylphenyl-5-(p-carboxymethylphenoxymethyl)oxazolidin-2-one in 20 ml of THF, and the mixture is stirred at room temperature for 24 h. 3-p-Aminomethylphenyl-5-(p-carboxymethylphenoxymethyl)oxazolidin-2-one Na salt is obtained, M.p. 286°–287°.

Example 5

0.17 ml of ethyldiisopropylamine is added to a solution of 0.2 g of 1-amidino-3,5-dimethylpyrazole nitrate in 17 ml of dioxane and 5 ml of water, and the mixture is stirred for 15 min. 0.4 g of 3-p-aminomethylphenyl- 5-(p-methoxycarbonylmethylphenoxymethyl)oxazolidin-2-one is subsequently added and the mixture is boiled for 30 h, concentrated by evaporation, and worked up in the customary manner. 3-p-Guanidinomethylphenyl-5-(p-methoxycarbonylmethylphenoxymethyl)oxazolidin-2-one is obtained.

The following are obtained in an analogous manner
with 3-p-aminomethylphenyl-5-(o-methoxycarbonylmethylphenoxymethyl)oxazolidin-2-one:
3-p-guanidinomethylphenyl-5-(o-methoxycarbonylmethylphenoxymethyl)oxazolidin-2-one;
with 3-p-aminomethylphenyl-5-(m-methoxycarbonylmethylphenoxymethyl)oxazolidin-2-one:
3-p-guanidinomethylphenyl-5-(m-methoxycarbonylmethylphenoxymethyl)oxazolidin-2-one;
with 3-p-aminomethylphenyl-5-[2,4-bis(methoxycarbonylmethyl)phenoxymethyl]oxazolidin-2-one:
3-p-guanidinomethylphenyl-5-[2,4-bis(methoxycarbonylmethyl)phenoxymethyl]oxazolidin-2-one;
with 3-p-aminomethylphenyl-5-[2,5-bis(methoxycarbonylmethyl)phenoxymethoyl]oxazolidin-2-one:
3-p-guanidinomethylphenyl-5-[2,5-bis(methoxycarbonylmethyl)phenoxymethyl]oxazolidin-2-one;
with 3-p-aminomethylphenyl-5-[2,6-bis(methoxycarbonylmethyl)phenoxymethyl]oxazolidin-2-one:
3-p-guanidinomethylphenyl-5-[2,6-bis(methoxycarbonylmethyl)phenoxymethyl]oxazolidin-2-one;
with 3-p-aminomethylphenyl-5-[3,4-bis(methoxycarbonylmethyl)phenoxymethyl]oxazolidin-2-one:
3-p-guanidinomethylphenyl-5-[3,4-bis(methoxycarbonylmethyl)phenoxymethyl]oxazolidin-2-one;
with 3-p-aminomethylphenyl-5-[3,5-bis(methoxycarbonylmethyl)phenoxymethyl]oxazolidin-2-one:
3-p-guanidinomethylphenyl-5-[3,5-bis(methoxycarbonylmethyl)phenoxymethyl]oxazolidin-2-one;
with 3-p-aminomethylphenyl-5-(2-methoxycarbonylmethylthien-4-yloxymethyl)oxazolidin-2-one:
3-p-guanidinomethylphenyl-5-(2-methoxycarbonylmethylthien-4-yloxymethyl)oxazolidin-2-one;
with 3-p-aminomethylphenyl-5-(3-methoxycarbonylmethylthien-4-yloxymethyl)oxazolidin-2-one:
3-p-guanidinomethylphenyl-5-(3-methoxycarbonylmethylthien-4-yloxymethyl)oxazolidin-2-one;
with 3-p-aminomethylphenyl-5-(2-methoxycarbonylmethylthien-3-yloxymethyl)oxazolidin-2-one:
3-p-guanidinomethylphenyl-5-(2-methoxycarbonylmethylthien-3-yloxymethyl)oxazolidin-2-one;
with 3-p-aminomethylphenyl-5-(2-methoxycarbonylmethylpyrrol-4-yloxymethyl)oxazolidin-2-one:
3-p-guanidinomethylphenyl-5-(2-methoxycarbonylmethylpyrrol-4-yloxymethyl)oxazolidin-2-one;
with 3-p-aminomethylphenyl-5-(3-methoxycarbonylmethylpyrrol-4-yloxymethyl)oxazolidin-2-one:
3-p-guanidinomethylphenyl-5-(3-methoxycarbonylmethylpyrrol-4-yloxymethyl)oxazolidin-2-one;
with 3-p-aminomethylphenyl-5-(2-methoxycarbonylmethyl-3-carboxypyrrol-yloxymethyl)oxazolidin-2-one:
3-p-guanidinoreethylphenyl-5-(2-methoxycarbonylmethyl-3-carboxypyrrol-4-yloxymethyl)oxazolidin-2-one;
with 3-p-aminomethylphenyl-5-(2-carboxy-5-methoxycarbonylmethylpyrrol-3-yloxymethyl)oxazolidin-2-one:
3-p-guanidinomethylphenyl-5-(2-carboxy-5-methoxycarbonylmethylpyrrol-3-yloxymethyl)oxazolidin-2-one.

Example 6

$H_2S$ gas is passed, at −10°, into a solution of 1.2 g of 3-p-cyanophenyl-5-(p-methoxycarbonylmethylphenoxymethyl)oxazolidin-2-one (obtainable in accordance with Example 1) in 50 ml of pyridine and 7 ml of triethylamine. The mixture is subsequently stirred at room temperature for 14 h and concentrated by evaporation; the residue is dissolved in 50 ml of acetone and treated with 9 ml of methyl iodide. After this mixture has been stirred for a further 6 h, it is filtered and the residue is washed with 5 ml of acetone and dissolved in 30 ml of methanol; 4.6 g of ammonium acetate are added to this solution, which is stirred at room temperature for 24 h. Following the customary working-up, 3-p-amidinophenyl-5-(p-methoxycarbonylmethylphenoxymethyl)oxazolidin-2-one (semihydriodide) is obtained, M.p. 151°–152°.

The following are obtained in an analogous manner
from 3-p-cyanophenyl-5-(o-methoxycarbonylmethylphenoxymethyl)oxazolidin-2-one:
3-p-amidinophenyl-5-(o-methoxycarbonylmethylphenoxymethyl)oxazolidin-2-one (hydriodide), $M^++1 =384$;
from 3-p-cyanophenyl-5-(m-methoxycarbonylmethylphenoxymethyl)oxazolidin-2-one:
3-p-amidinophenyl-5-(m-methoxycarbonylmethylphenoxymethyl)oxazolidin-2-one (hydriodide), $M^+1=384$;
from 3-p-cyanophenyl-5-[2,4-bis(methoxycarbonylmethyl)phenoxymethyl]-oxazolidin-2-one:
3-p-amidinophenyl-5-[2,4-bis(methoxycarbonylmethyl)phenoxymethyl]-oxazolidin-2-one;
from 3-p-cyanophenyl-5-[2,5-bis(methoxycarbonylmethyl)phenoxymethyl]-oxazolidin-2-one:
3-p-amidinophenyl-5-[2,5-bis(methoxycarbonylmethyl)phenoxymethyl]-oxazolidin-2-one;
from 3-p-cyanophenyl-5-[2,6-bis(methoxycarbonylmethyl)phenoxymethyl]-oxazolidin-2-one:
3-p-amidinophenyl-5-[2,6-bis(methoxycarbonylmethyl)phenoxymethyl]-oxazolidin-2-one;
from 3-p-cyanophenyl-5-[3,4-bis(methoxycarbonylmethyl)phenoxymethyl]-oxazolidin-2-one:
3-p-amidinophenyl-5-[3,4-bis(methoxycarbonylmethyl)phenoxymethyl]-oxazolidin-2-one;
from 3-p-cyanophenyl-5-[3,5-bis(methoxycarbonylmethyl)phenoxymethyl]-oxazolidin-2-one:
3-p-amidinophenyl-5-[3,5-bis(methoxycarbonylmethyl)phenoxymethyl]-oxazolidin-2-one;
from 3-p-cyanophenyl-5-(2-methoxycarbonylmethylthien-4-yloxymethyl)oxazolidin-2-one:
3-p-amidinophenyl-5-(2-methoxycarbonylmethylthien-4-yloxymethyl)oxazolidin-2-one;

from 3-p-cyanophenyl-5-(3-methoxycarbonylmethylthien-4-yloxymethyl)oxazolidin-2-one:
3-p-amidinophenyl-5-(3-methoxycarbonylmethylthien-4-yloxymethyl)oxazolidin-2-one;
from 3-p-cyanophenyl-5-(2-methoxycarbonylmethylthien-3-yloxymethyl)oxazolidin-2-one:
3-p-amidinophenyl-5-(2-methoxycarbonylmethylthien-3-yloxymethyl)oxazolidin-2-one;
from 3-p-cyanophenyl-5-(2-methoxycarbonylmethylpyrrol-4-yloxymethyl)oxazolidin-2-one:
3-p-amidinophenyl-5-(2-methoxycarbonylmethylpyrrol-4-yloxymethyl)oxazolidin-2-one;
from 3-p-cyanophenyl-5-(3-methoxycarbonylmethylpyrrol-4-yloxymethyl)oxazolidin-2-one:
3-p-amidinophenyl-5-(3-methoxycarbonylmethylpyrrol-4-yloxymethyl)oxazolidin-2-one;
from 3-p-cyanophenyl-5-(2-methoxycarbonylmethyl-3-carboxypyrrol-4-yloxymethyl)oxazolidin-2-one:
3-p-amidinophenyl-5-(2-methoxycarbonylmethyl-3-carboxypyrrol-4-yloxymethyl) oxazolidin-2-one;
from 3-p-cyanophenyl-5-(2-carboxy-5-methoxycarbonylmethylpyrrol-3-yl-oxymethyl)oxazolidin-2-one:
3-p-amidinophenyl-5-(2-carboxy-5-methoxycarbonylmethylpyrrol-3-yloxymethyl)oxazolidin-2-one.

Example 7

The following carboxylic acids are obtained, in analogy with Example 3, by hydrolyzing the corresponding esters from Example 6:

3-p-amidinophenyl-5-(p-carboxymethylphenoxymethyl)oxazolidin-2-one, M.p. 281°;

3-p-amidinophenyl-5-(o-carboxymethylphenoxymethyl)oxazolidin-2-one, M.p. 274°;

3-p-amidinophenyl-5-(m-carboxymethylphenoxymethyl)oxazolidin-2-one (hydrochloride), M.p. 271°;

3-p-amidinophenyl-5-[2,4-bis(carboxymethyl)phenoxymethyl]oxazolidin-one;

3-p-amidinophenyl-5-[2,5-bis(carboxymethyl)phenoxymethyl]oxazolidin-one;

3-p-amidinophenyl-5-[2,6-bis(carboxymethyl)phenoxymethyl]oxazolidin-one;

3-p-amidinophenyl-5-[3,4-bis(carboxymethyl)phenoxymethyl]oxazolidin-one;

3-p-amidinophenyl-5-[3,5-bis(carboxymethyl)phenoxymethyl]oxazolidin-one;

3-p-amidinophenyl-5-(2-carboxymethylthien-4-yloxymethyl)oxazolidin-2-one;

3-p-amidinophenyl-5-(3-carboxymethylthien-4-yloxymethyl)oxazolidin-2-one;

3-p-amidinophenyl-5-(2-carboxymethylthien-3-yloxymethyl)oxazolidin-2-one;

3-p-amidinophenyl-5-(2-carboxymethylpyrrol-4-yloxymethyl)oxazolidin-2-one;

3-p-amidinophenyl-5-(3-carboxymethylpyrrol-4-yloxymethyl)oxazolidin-2-one;

3-p-amidinophenyl-5-(2-carboxymethyl-3-carboxypyrrol-4-yloxymethyl)-oxazolidin-2-one;

3-p-amidinophenyl-5-(2-carboxy-5-carboxymethylpyrrol-3-yloxymethyl)oxazolidin-2-one.

Example 8

The following carboxylic acids are obtained, in analogy with Example 3, by hydrolyzing the corresponding esters from Example 5:

3-p-guanidinomethylphenyl-5-(p-carboxymethylphenoxymethyl)oxazolidin-2-one, M.p.>300°;

3-p-guanidinomethylphenyl-5-(o-carboxymethylphenoxymethyl)oxazolidin-2-one;

3-p-guanidinomethylphenyl-5-(m-carboxymethylphenoxymethyl)oxazolidin-2-one;

3-p-guanidinomethylphenyl-5-[2,4-bis(carboxymethyl)phenoxymethyl]-oxazolidin-2-one;

3-p-guanidinomethylphenyl-5-[2,5-bis(carboxymethyl)phenoxymethyl]-oxazolidin-2-one;

3-p-guanidinomethylphenyl-5-[2,6-bis(carboxymethyl)phenoxymethyl]-oxazolidin-2-one;

3-p-guanidinomethylphenyl-5-[3,4-bis(carboxymethyl)phenoxymethyl]-oxazolidin-2-one;

3-p-guanidinomethylphenyl-5-[3,5-bis(carboxymethyl)phenoxymethyl]-oxazolidin-2-one;

3-p-guanidinomethylphenyl-5-(2-carboxymethylthien-4-yloxymethyl)-oxazolidin-2-one;

3-p-guanidinomethylphenyl-5-(3-carboxymethylthien-4-yloxymethyl)-oxazolidin-2-one;

3-p-guanidinomethylphenyl-5-(2-carboxymethylthiophen-3-yloxymethyl)-oxazolidin-2-one;

3-p-guanidinomethylphenyl-5-(2-carboxymethylpyrrol-4-yloxymethyl)-oxazolidin-2-one;

3-p-guanidinomethylphenyl-5-(3-carboxymethylpyrrol-4-yloxymethyl)-oxazolidin-2-one;

3-p-guanidinomethylphenyl-5-(2-carboxymethyl-3-carboxypyrrol-4-yloxymethyl)-oxazolidin-2-one;

3-p-guanidinomethylphenyl-5-(2-carboxy-5-carboxymethylpyrrol-3-yloxymethyl)oxazolidin-2-one.

Example 9

3-p-Cyanophenyl-5-(p-methoxycarbonylmethylphenylthiomethyl)oxazolidin-2-one is obtained, in analogy with Example 1, proceeding from Na p-methoxycarbonylmethylthiophenoxide (obtainable by converting p-mercaptobenzyl cyanide into the corresponding carboxylic acid, esterifying with methanol to give p-methoxycarbonylmethylthiophenol and subsequently converting the latter into the thiophenoxide), by reaction with 3-p-cyanophenyl-5-methane-sulfonyloxymethyloxazolidin-2-one ("A") (obtainable in accordance with Example 1).

The following can be obtained in an analogous manner by reaction of "A"
with Na o-methoxycarbonylmethylthiophenoxide:
3-p-cyanophenyl-5-(o-methoxycarbonylmethylphenylthiomethyl)oxazolidin-2-one;
with Na m-methoxycarbonylmethylthiophenoxide:
3-p-cyanophenyl-5-(m-methoxycarbonylmethylphenylthiomethyl)oxazolidin-2-one;
with Na 2,4-bis(methoxycarbonylmethyl)thiophenoxide:
3-p-cyanophenyl-5-[2,4-bis(methoxycarbonylmethyl)phenylthiomethyl]-oxazolidin-2-one;
with Na 2,5-bis(methoxycarbonylmethyl)thiophenoxide:
3-p-cyanophenyl-5-[2,5-bis(methoxycarbonylmethyl)phenylthiomethyl]-oxazolidin-2-one;
with Na 2,6-bis(methoxycarbonylmethyl)thiophenoxide:
3-p-cyanophenyl-5-[2,6-bis(methoxycarbonylmethyl)phenylthiomethyl]-oxazolidin-2-one;
with Na 3,4-bis(methoxycarbonylmethyl)thiophenoxide:
3-p-cyanophenyl-5-[3,4-bis(methoxycarbonylmethyl)phenylthiomethyl]-oxazolidin-2-one;

with Na 3,5-bis(methoxycarbonylmethyl)thiophenoxide:
3-p-cyanophenyl-5-[3,5-bis(methoxycarbonylmethyl)phenylthiomethyl]-oxazolidin-2-one;
with 2-methoxycarbonylmethyl-4-hydroxythiophene Na salt:
3-p-cyanophenyl-5-(2-methoxycarbonylmethylthien-4-yloxymethyl)oxazolidin-2-one;
with 3-methoxycarbonylmethyl-4-hydroxythiophene Na salt:
3-p-cyanophenyl-5-(3-methoxycarbonylmethylthien-4-yloxymethyl)oxazolidin-2-one;
with 2-methoxycarbonylmethyl-3-hydroxythiophene Na salt:
3-p-cyanophenyl-5-(2-methoxycarbonylmethylthien-3-yloxymethyl)oxazolidin-2-one;
with 2-methoxycarbonylmethyl-4-hydroxypyrrole Na salt:
3-p-cyanophenyl-5-(2-methoxycarbonylmethylpyrrol-4-yloxymethyl)oxazolidin-2-one;
with 3-methoxycarbonylmethyl-4-hydroxypyrrole Na salt:
3-p-cyanophenyl-5-(3-methoxycarbonylmethylpyrrol-4-yloxymethyl)oxazolidin-2-one;
with 2-methoxycarbonylmethyl-3-carboxy-4-hydroxypyrrole Na salt:
3-p-cyanophenyl-5-(2-methoxycarbonylmethyl-3-carboxypyrrol-4-yloxymethyl)oxazolidin-2-one;
with 2-carboxy-3-hydroxy-5-methoxycarbonylmethylpyrrole Na salt:
3-p-cyanophenyl-5-(2-carboxy-5-methoxycarbonylmethylpyrrol-3-yloxymethyl)oxazolidin-2-one.

Example 10

The following amidinophenyloxazolidin-2-one derivatives are obtained in analogy with Example 6, proceeding from the nitriles from Example 9:

3-p-amidinophenyl-5-(p-methoxycarbonylmethylphenylthiomethyl)oxazolidin-2-one;

3-p-amidinophenyl-5-(o-methoxycarbonylmethylphenylthiomethyl)oxazolidin-2-one;

3-p-amidinophenyl-5-(m-methoxycarbonylmethylphenylthiomethyl)oxazolidin-2-one;

3-p-amidinophenyl-5-[2,4-bis(methoxycarbonylmethyl)phenylthiomethyl]-oxszolidin-2-one;

3-p-amidinophenyl-5-[2,5-bis(methoxycarbonylmethyl)phenylthiomethyl]-oxazolidin-2-one;

3-p-amidinophenyl-5-[2,6-bis(methoxycarbonylmethyl)phenylthiomethyl]-oxazolidin-2-one;

3-p-amidinophenyl-5-[3,4-bis(methoxycarbonylmethyl)phenylthiomethyl]-oxszolidin-2-one;

3-p-amidinophenyl-5-[3,5-bis(methoxycarbonylmethyl)phenylthiomethyl]-oxazolidin-2-one;

3-p-amidinophenyl-5-(2-methoxycarbonylmethylthien-4-yloxymethyl)oxazolidin-2-one;

3-p-smidinophenyl-5-(3-methoxycarbonylmethylthien-4-yloxymethyl)oxazolidin-2-one;

3-p-amidinophenyl-5-(2-methoxycarbonylmethylthien-3-yloxymethyl)oxazolidin-2-one;

3-p-amidinophenyl-5-(2-methoxycarbonylmethylpyrrol-4-yloxymethyl)oxazolidin-2-one;

3-p-amidinophenyl-5-(3-methoxycarbonylmethylpyrrol-4-yloxymethyl)oxazolidin-2-one;

3-p-amidinophenyl-5-(2-methoxycarbonylmethyl-3-carboxypyrrol-4-yloxymethyl) oxazolidin-2-one;

3-p-amidinophenyl-5-(2-carboxy-5-methoxycarbonylmethylpyrrol-3-yloxymethyl)oxazolidin-2-one.

Example 11

The following carboxylic acids are obtained in analogy with Example 3 by hydrolyzing the corresponding esters from Example 10:

3-p-amidinophenyl-5-(p-carboxymethylphenylthiomethyl)oxazolidin-2-one;

3-p-amidinophenyl-5-(o-carboxymethylphenylthiomethyl)oxazolidin-2-one;

3-p-amidinophenyl-5-(m-carboxymethylphenylthiomethyl)oxazolidin-2-one;

3-p-amidinophenyl-5-[2,4-bis(carboxymethyl)phenylthiomethyl]oxazolidin-2-one;

3-p-amidinophenyl-5-[2,5-bis(carboxymethyl)phenylthiomethyl]oxazolidin-2-one;

3-p-amidinophenyl-5-[2,6-bis(carboxymethyl)phenylthiomethyl]oxazolidin-2-one;

3-p-amidinophenyl-5-[3,4-bis(carboxymethyl)phenylthiomethyl]oxazolidin-2-one;

3-p-amidinophenyl-5-[3,5-bis(carboxymethyl)phenylthiomethyl]oxazolidin-2-one;

3-p-amidinophenyl-5-(2-carboxymethylthiophen-4-yloxymethyl)oxazolidin-2-one;

3-p-amidinophenyl-5-(3-carboxymethylthiophen-4-yloxymethyl)oxazolidin-2-one;

3-p-amidinophenyl-5-(2-carboxymethylthiophen-3-yloxymethyl)oxazolidin-2-one;

3-p-amidinophenyl-5-(2-carboxymethylpyrrol-4-yloxymethyl)oxazolidin-2-one;

3-p-amidinophenyl-5-(3-carboxymethylpyrrol-4-yloxymethyl)oxazolidin-2-one;

3-p-amidinophenyl-5-(2-carboxymethyl-3-carboxypyrrol-4-yloxymethyl)-oxazolidin-2-one;

3-p-amidinophenyl-5-(2-carboxy-5-carboxymethylpyrrol-3-yloxymethyl)-oxazolidin-2-one.

Example 12

3-p-Cyanophenyl-5-(p-methoxycarbonylmethylphenylaminomethyl)oxazolidin-2-one is obtained in analogy with Example 1, proceeding from pomethoxycarbonylmethylaniline (obtainable by converting p-aminobenzyl cyanide into p-aminophenylacetic acid and esterifying the latter with methanol), by reaction with 3-p-cyanophenyl-5-methanesulfonyloxymethyloxazolidin-2-one ("A") (obtainable in accordance with Example 1).

The following are obtained in an analogous manner by reaction of "A"
with o-methoxycarbonylmethylaniline:
3-p-cyanophenyl-5-(o-methoxycarbonylmethylphenylaminomethyl)oxazolidin-2-one;
with m-methoxycarbonylmethylaniline:
3-p-cyanophenyl-5-(m-methoxycarbonylmethylphenylaminomethyl)oxazolidin-2-one;
with 2,4-bis(methoxycarbonylmethyl)aniline:
3-p-cyanophenyl-5-[2,4-bis(methoxycarbonylmethyl)phenylaminomethyl]oxazolidin-2-one;
with 2,5-bis(methoxycarbonylmethyl)aniline:
3-p-cyanophenyl-5-[2,5-bis(methoxycarbonylmethyl)phenylaminomethyl]oxazolidin-2-one;
with 3,4-bis(methoxycarbonylmethyl)aniline:
3-p-cyanophenyl-5-[3,4-bis(methoxycarbonylmethyl)phenylaminomethyl]oxazolidin-2-one.

Example 13

The following amidinophenyloxazolidin-2-one derivatives are obtained in analogy with Example 6, proceeding from the nitriles from Example 9:

3-p-amidinophenyl-5-(p-methoxycarbonylmethylphenylaminomethyl)oxazolidin-2-one;

3-p-amidinophenyl-5-(o-methoxycarbonylmethylphenylaminomethyl)oxazolidin-2-one;

3-p-amidinophenyl-5-(m-methoxycarbonylmethylphenylaminomethyl)oxazolidin-2-one;

3-p-amidinophenyl-5-[2,4-bis(methoxycarbonylmethyl)phenylaminomethyl]oxazolidin-2-one;

3-p-amidinophenyl-5-[2,5-bis(methoxycarbonylmethyl)phenylaminomethyl]oxazolidin-2-one;

3-p-amidinophenyl-5-[3,4-bis(methoxycarbonylmethyl)phenylaminomethyl]oxazolidin-2-one.

Example 14

The following carboxylic acids are obtained in analogy with Example 3 by hydrolyzing the corresponding esters from Example 13:

3-p-amidinophenyl-5-(p-carboxymethylphenylaminomethyl)oxazolidin-2-one;

3-p-amidinophenyl-5-(o-carboxymethylphenylaminomethyl)oxazolidin-2-one;

3-p-amidinophenyl-5-(m-carboxymethylphenylaminomethyl)oxazolidin-2-one;

3-p-amidinophenyl-5-[2,4-bis(carboxymethyl)phenylaminomethyl]oxazolidin-2-one;

3-p-amidinophenyl-5-[2,5-bis(carboxymethyl)phenylaminomethyl]oxazolidin-2-one;

3-p-amidinophenyl-5-[3,4-bis(carboxymethyl)phenylaminomethyl]oxazolidin-2-one.

Example 15

3-p-Cyanophenyl-5-(p-methoxycarbonylmethylphenyl-N-methylaminomethyl)oxazolidin-2-one is obtained in analogy with Example 1, proceeding from p-methoxycarbonylmethyl-N-methylaniline (obtainable by converting p-N-methylaminobenzyl cyanide into p-methylaminophenylacetic acid and esterifying the latter with methanol), by reaction with 3-p-cyanophenyl-5-methanesulfonyloxymethyloxazolidin-2-one ("A") (obtainable in accordance with Example 1).

Example 16

3-p-Amidinophenyl-5-(p-methoxycarbonylmethylphenyl-N-methylamino-methyl)oxazolidin-2-one is obtained in analogy with Example 6, proceeding from nitrile from Example 15.

Example 17

3-p-Amidinophenyl-5-(p-carboxymethylphenyl-N-methylaminomethyl)oxazolidin-2-one is obtained in analogy with Example 3 by hydrolyzing the ester from Example 16.

The following examples relate to pharmaceutical preparations.

Example A: Injection Vials

A solution of 100 g of an active compound of the formula I and 5 g of disodium hydrogen phosphate in 3 l of doubly distilled water is adjusted to pH 6.5 with 2N hydrochloric acid, filtered sterile, filled into injection vials and lyophilized, and the vials are sealed in a sterile manner. Each injection vial contains 5 mg of active compound.

Example B: Suppositories

A mixture of 20 mg of an active compound of the formula I is fused with 100 g of soya lecithin and 1400 g of cocoa butter, and the mixture is poured into molds and allowed to cool. Each suppository contains 20 mg of active compound.

Example C: Solution

A solution of 1 g of an active compound of the formula I, 9.38 g of $NaH_2PO_4.2H_2O$, 28.48 g of $Na_2HPO_4.12H_2O$ and 0.1 g of benzalkonium chloride is prepared in 940 ml of doubly distilled water. The solution is adjusted to pH 6.8, made up to 1 l and sterilized by irradiation. This solution can be used in the form of eye drops.

Example D: Ointment 500 mg of an active compound of the formula I are mixed with 99.5 g of petroleum jelly under aseptic conditions.

Example E: Tablets

A mixture of 1 kg of active compound of the formula I, 4 kg of lactose, 1.2 kg of potato starch, 0.2 kg of talc and 0.1 kg of magnesium stearate is pressed to give tablets in a customary manner, such that each tablet contains 10 mg of active compound.

Example F: Coated Tablets

Tablets are pressed analogously to Example E and then coated in a customary manner with a coating of sucrose, potato starch, talc, tragacanth and colorant.

Example G: Capsules

Hard gelatin capsules are filled with 2 kg of active compound of the formula I in the customary manner, such that each capsule contains 20 mg of active compound.

Example H: Ampoules

A solution of 1 kg of active compound of the formula I in 60 l of doubly distilled water is filled into ampoules and lyophilized under sterile conditions, and the ampoules are sealed in a sterile manner. Each ampoule contains 10 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An oxazolidinone derivative of formula I

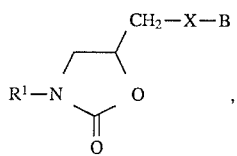

wherein $R^1$ is a phenyl radical which is unsubstituted or is monosubstituted by X is —NH— or —NA—;

B is

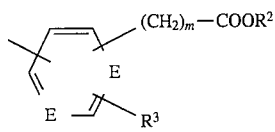

o

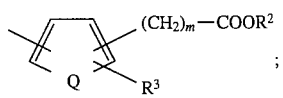

A is $C_{1-6}$-alkyl;

$R^2$ is H, A, Li, Na, K, $NH_4$ or benzyl;

$R^3$ is H or —$(CH_2)_n$—$COOR^2$;

E is, in each case —CH—;

Q is —NH—;

m is 1, 2 or 3; and n is 0, 1, 2 or 3;

or a physiologically compatible salt thereof.

2. A compound of claim 1, which is a D form enantiomer.

3. A compound of claim 1, which is an L form enantiomer.

4. A compound of claim 1, wherein A is $C_{1-4}$-alkyl.

5. A compound of claim 1, wherein X is —NH— or —$NCH_3$.

6. A compound of claim 1, wherein B is:

2-carboxymethylphenyl, 3-carboxymethylphenyl, 4-carboxymethylphenyl, 2-methoxycarbonylphenyl, 3-methoxycarbonylphenyl, 4-methoxycarbonylphenyl, 2-ethoxycarbonylphenyl, 3-ethoxycarbonylphenyl, 4-ethoxycarbonylphenyl, 2-carboxymethylthien-4-yl, 2-carboxymethylpyrrol-4-yl, 3-carboxymethylpyrrol-4-yl, 2,5-dicarboxymethylpyrrol-4-yl, 2,3-dicarboxymethylpyrrol-4-yl, 2-carboxymethyl-3-carboxypyrrol-4-yl, 2-carboxymethyl-5-carboxypyrrol-4-yl, 2,3-dicarboxymethylphenyl, 2,4-dicarboxymethylphenyl, 2,5-dicarboxymethylphenyl, 2,6-dicarboxymethylphenyl, 3,4-dicarboxymethylphenyl, 3,5-dicarboxymethylphenyl, or a methyl or ethyl ester thereof, or a Li, Na, K or ammonium salt thereof.

7. A compound of claim 1, wherein $R^2$ is H, A or Na.

8. A compound of claim 1, wherein $R^3$ is H or carboxymethyl.

9. A compound of claim 1, wherein Q is —S— or —NH—.

10. A compound of claim 1, wherein m and n are each 1.

11. A pharmaceutical composition comprising an effective amount of a compound of claim 1 and a pharmaceutically acceptable excipient.

12. A composition of claim 11, wherein said composition comprises 5 mg–1 g of said compound.

13. A compound of claim 1, which inhibits the binding of fibrinogen to fibrinogen receptor.

* * * * *